US00PP11074P

United States Patent [19]

Fuess

[11] Patent Number: Plant 11,074

[45] Date of Patent: Sep. 28, 1999

[54] CHRYSANTHEMUN PLANT NAMED 'EMPIRE COGNAC'

[76] Inventor: Janet S. Fuess, 22 Country Club Dr., New York Mills, N.Y. 13417

[21] Appl. No.: 09/035,577

[22] Filed: Mar. 6, 1998

[51] Int. Cl.[6] ..... A01H 5/00

[52] U.S. Cl. ..... Plt./290

[58] Field of Search ..... Plt./287, 289, 290

*Primary Examiner*—Howard J. Locker

*Attorney, Agent, or Firm*—Foley & Lardner

[57] ABSTRACT

A new and distinct cultivar of Chrysanthemum plant named 'Empire Cognac', characterized particularly by its two-tone yellow-bronze, spoon-tipped ray florets; fully double flowers, with no disc florets; 4.25–4.75 cm capitulum diameter; fully expanded ray florets, approximately 2.0–2.25 cm long and 0.5 cm wide; 7 week flower response in light/shade programs; good performance in outdoor gardens, with natural season flowering date of September 12; and compact cushion habit.

1 Drawing Sheet

The present invention comprises a new and distinct cultivar of *Dendranthema grandiflora,* referred to by the cultivar name 'Empire Cognac'.

'Empire Cognac' is a product of a planned breeding program which had the objective of creating new Chrysanthemum cultivars with freely branching, compact cushion habit, early flower response, two-tone bronze decorative flowers and adaptability as a garden variety. Such traits in combination were not present in previously available commercial cultivars.

'Empire Cognac' was originated from a hybridization made by the inventor in a controlled breeding program in New Hartford, N.Y. in 1993. The female parent was 'Empire Cheyenne', an orange-bronze decorative disclosed in U.S. Plant Pat. No. 8,973. The male parent of 'Empire Cognac' was a cultivar identified as C89-14, a proprietary breeding line.

'Empire Cognac' was discovered and selected as one flowering plant within the progeny of the stated parentage by the inventor in September 1994 in a controlled environment in New Hartford, N.Y.

The first act of asexual reproduction of 'Empire Cognac' was accomplished when vegetative cuttings were taken by the inventor from the initial selection in October 1994 in a controlled environment in New Hartford, N.Y. Horticultural examination of selected units initiated in September 1995 has demonstrated that the combination of characteristics as herein disclosed for 'Empire Cognac' are firmly fixed and are retained through successive generations of asexual reproduction.

'Empire Cognac' has not been observed under all possible environmental conditions. The phenotype may vary significantly with variations in environment such as temperature, light intensity, and day length, without, however, any variation in genotype. The following observations, measurements and comparisons describe plants grown in New Hartford, N.Y. under natural outdoor conditions which approximate those generally used in commerical practice.

The following traits have been repeatedly observed and are determined to be basic characteristics of 'Empire Cognac', which in combination distinguish this chrysanthemum as a new and distinct cultivar:

1. Two-tone yellow-bronze ray florets, spoon-tipped.
2. An average of 256 ray florets.
3. Fully double flowers, with no disc florets.
4. Capitulum approximately 4.25–4.75 cm in diameter.
5. Fully expanded ray florets are approximately 2.0–2.25 cm long and 0.5 cm wide.
6. 7 week flower response in light/shade programs.

7. Performs well in the outdoor garden, with a natural season flowering date of September 12 in New Hartford, N.Y.
8. Compact, cushion habit, making it suitable for production in 4–8" containers or in the garden.

Of the many commerical cultivars known to the inventor, the most similar in comparison to 'Empire Cognac' is 'Empire Scottsdale', disclosed in U.S. Plant Pat. No. 9,934. In comparison to 'Empire Scottsdale', 'Empire Cognac' has a 1 week earlier response in light/shade programs, blooms approxaimtely 2 weeks earlier in natural season, is slightly taller, capitulum has a more pronounced bicolor effect, and has spoon-tipped ray florets. The parentage of the two cultivars is the same. Botanical characteristics such as capitulum size, the fully double flowers, general tonality (bronze) and adapability to greenhouse or outdoor cultures are similar to those same characteristics of 'Empire Scottsdale'.

The accompanying photographic drawing comprises a top perspective view showing typical flower and foliage characteristics of 'Empire Cognac', with colors being as nearly true as possible with illustrations of this type.

In the following description color references are made to The Royal Horticultural Society Colour Chart. The color values were determined between 11:00 am and 1:00 pm on Sep. 23, 1997 under 4,000 footcandles at New Hartford, N.Y.

Classification:

*Botanical.*—*Dendranthema grandiflora,* cv. 'Empire Cognac'.

*Commercial.*—Decorative garden mum.

Inflorescence:

*Capitulum.*—Form: Flat. Type: Double. Diameter across face: 4.25–4.75 cm.

*Corolla of ray florets.*—Color (general tonality from a distance of three meters. Bronze. Color (under surface): 31C. Color (upper surface): 22C, darkening to 34A at center of capitulum.

*Corolla of disc florets.*—No disc florets.

*Reproductive organs.*—Androecium: None. Gynoecium. Present on ray florets; style 0.4 cm, bifurcated.

Plant:

*General appearance.*—Height: 25–35 cm, when grown in 8" pot, outdoors, with no growth regulators.

*Foliage.*—Color (upper surface): 139A. Color (under surface): 137B . Shape: 6.5–7.5 cm long, 4.5–5.0 cm wide, 5-lobed.

It is claimed:

1. A new and distinct cultivar of Chrysanthemum plant named 'Empire Cognac', as illustrated and described.

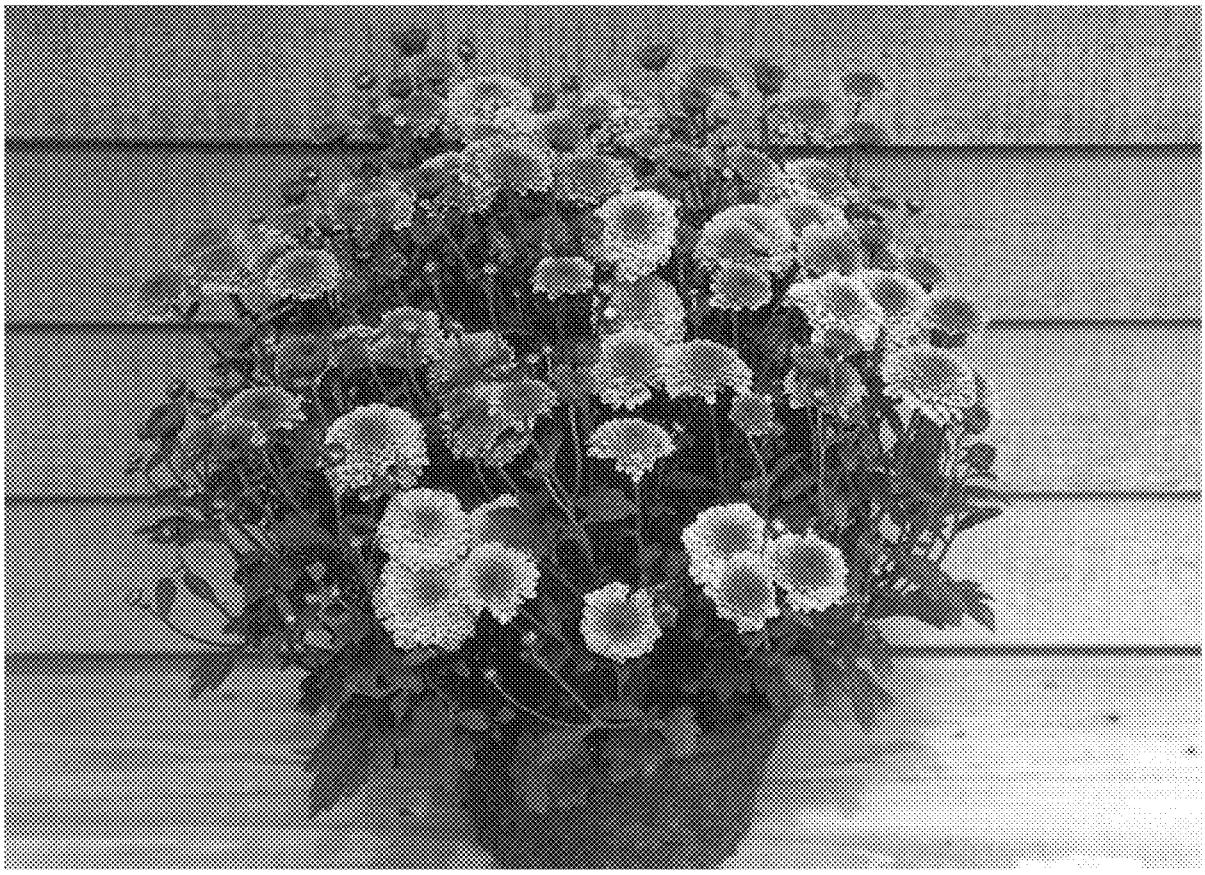

* * * * *